United States Patent [19]

Tuba et al.

[11] 4,110,326
[45] Aug. 29, 1978

[54] ACYLATED DIEPOXY-ANDROSTANE AND A PROCESS FOR THE PREPARATION THEREOF

[75] Inventors: Zoltan Tuba; Maria Marsai, both of Budapest, Hungary

[73] Assignee: Richter Gedeon Vegyeszeti Gyar Rt, Budapest, Hungary

[21] Appl. No.: 762,233

[22] Filed: Jan. 25, 1977

Related U.S. Application Data

[63] Continuation-in-part of Ser. No. 702,050, Jul. 2, 1976, abandoned, and a continuation-in-part of Ser. No. 702,051, Jul. 2, 1976, abandoned, and a continuation-in-part of Ser. No. 709,325, Jul. 28, 1976, Pat. No. 4,071,515, and a continuation-in-part of Ser. No. 709,323, Jul. 28, 1976, Pat. No. 4,071,515.

[30] Foreign Application Priority Data

Jul. 15, 1975 [HU] Hungary ................................. 572

[51] Int. Cl.² ........................ C07J 71/00; C07J 43/00
[52] U.S. Cl. ........................... 260/239.55 R; 260/397; 260/397.5; 260/239.5
[58] Field of Search .................... 260/239.55 R, 239.55

[56] References Cited

U.S. PATENT DOCUMENTS 3,553,212  1/1971  Hewett et al. ................... 260/239.5

FOREIGN PATENT DOCUMENTS 1,398,050  6/1975  United Kingdom ............... 260/239.5

Primary Examiner—Elbert L. Roberts
Attorney, Agent, or Firm—Karl F. Ross

[57] ABSTRACT

A compound of the formula (I)

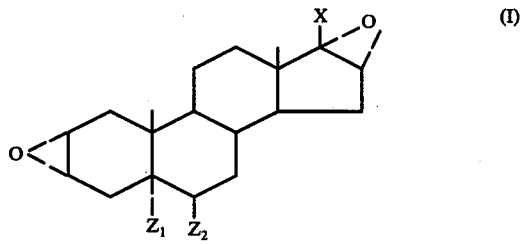

wherein
X is a halogen,
$Z_1$ and $Z_2$ are both hydrogen, or
$Z_1$ is hydroxy and $Z_2$ is chlorine, or
$Z_1$ and $Z_2$ together stand for an α-epoxy group.

24 Claims, No Drawings

ACYLATED DIEPOXY-ANDROSTANE AND A PROCESS FOR THE PREPARATION THEREOF

CROSS-REFERENCE TO RELATED APPLICATIONS

This application is a continuation-in-part of Ser. No. 702,050 filed July 2, 1976 (now abandoned) and a C-I-P to commonly owned applications Ser. No. 702,051 filed July 2, 1976, (now abandoned) Ser. No. 709,325 pending filed July 28, 1976, now Pat. No. 4,071,515 and Ser. No. 709,323 filed July 28, 1976.

The invention relates to new epoxy-androstanes of the formula (I)

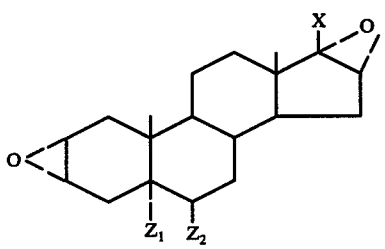

wherein
X is a halogen,
$Z_1$ and $Z_2$ are both hydrogen, or
$Z_1$ is hydroxy and $Z_2$ is chlorine, or
$Z_1$ and $Z_2$ together form an α-epoxy group. The invention relates as well to a process for the preparation of these compounds.

The new compounds of the formula (I) are valuable intermediate products in the synthesis of new steroid compound having curare-like activity (see application Ser. No. 709,323 and Ser. No. 709,325 mentioned above).

The compounds of the formula (I) are prepared according to the invention by reacting a compound of the formula (V)

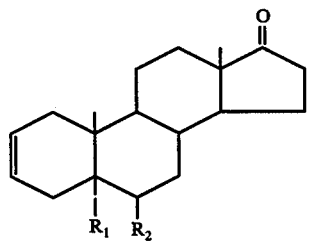

wherein $R_1$ and $R_2$ are both hydrogen or both hydroxy, with hydrazine, treating the obtained compound of the formula (IV)

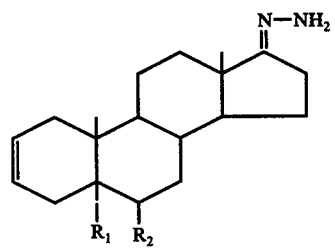

with an N-halo-succinimide to yield the corresponding compound of the formula (III)

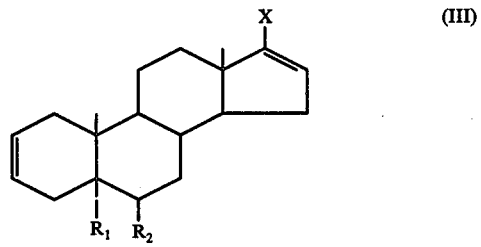

and then
(a) reacting a compound of the formula (III), wherein $R_1$ and $R_2$ are both hydrogen, with an organic peracid to yield a product of the formula (I), wherein $Z_1$ and $Z_2$ are both hydrogen; or
(b) reacting a compound of the formula (III), wherein $R_1$ and $R_2$ are both hydroxy, with an organic sulfonic acid chloride, preferably with methane sulfonic acid
chloride in the presence of an organic tertiary base to yield a mixture of the corresponding compounds of the formulae (IIA) and (IIB)

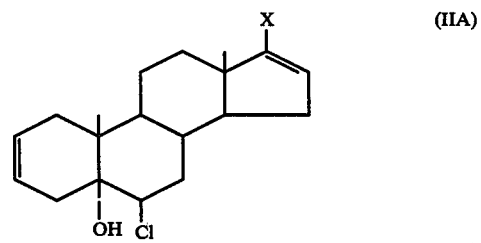

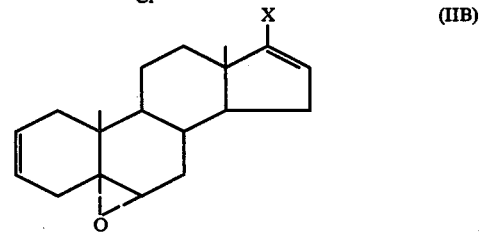

and then treating the mixture of the compounds of the formula (IIA) and (IIB)
(b$_1$) with a hydrohalic acid and subsequently with an organic paracid to yield a product of the formula (I), wherein $Z_1$ is hydroxy and $Z_2$ is chlorine,
(b$_2$) or with a base and subsequently with an organic peracid to yield a product of the formula (I), wherein $Z_1$ and $Z_2$ together are an α-epoxy group.

The starting compounds of the formula (V) are known substances; they are described e.g. in the Hungarian patent Specification No. 165,600; J. Org. Chem. 20, 542–545 (1955); Tetrahedron Letters 27, 1517–1526 (1971).

The intermediate compounds of the synthesis, the compounds of the formulas IV, III, IIA and IIB are new products not described in the literature hitherto.

The first step of the process of the invention, the preparation of the hydrazone of the formula (IV) is performed preferably in the following way:

The starting compound of the formula (V) is dissolved in a solvent of the lower alcohol type (e.g. $C_1$ to $C_6$ aliphatic alcohol), preferably in ethanol and is then reacted in the presence of a tertiary base, preferably triethylamine (i.e. a tertiary amine), at elevated temperature, preferably at the boiling point of the reaction mixture, with hydrazine hydrate. The reaction mixture is then poured into water and the thus obtained crude intermediate product of the formula (IV) is isolated and, if desired, purified by triturating with ether and-or recrystallizing from an apolar solvent, preferably from n-hexane.

The conversion of the thus-obtained androstene hydrazone of the formula (IV) into the 17-halo-androstene derivative of the formula (III) may be performed as follows:

The hydrazone of the formula (IV) is dissolved in an inert organic solvent, preferably in pyridine, the solution is cooled to a temperature between −30° and 20° C, preferably between −15° and 5° C and an N-halosuccinimide, preferably N-bromo-succinimide is added thereto. The reaction mixture is stirred until nitrogen evolution ceases and then is poured into water containing an equivalent amount (calculated on the basis of formula IV) of a nonoxidizing acid. The reaction product containing the desired compound of the formula (III) and, as by-product, a bis-steroid of the azine-type, is then extracted with an organic solvent, preferably with a halogenated hydrocarbon, such as carbon tetrachloride, or with an ether, e.g. with diethyl ether. The separated extract is washed to neutrality and the separated organic phase is evaporated. The evaporation residue is triturated with an apolar solvent, preferably with n-hexane, the insoluble by-product is filtered off and the filtrate is evaporated. The evaporation residue contains the crude compound of the formula (III), which is then purified by triturating with a mixture of ethanol and acetone.

The further conversion of the obtained compounds of the formula (III) into the desired end products of the formula (I) can be performed in two slightly different ways, depending on the meanings of $R_1$ and $R_2$ in the formula (III) and on the desired meaning of $Z_1$ and $Z_2$ in the end product of the formula (I):

(a) Compounds of the formula (III), wherein both $R_1$ and $R_2$ are hydrogen, can be converted directly into the corresponding diepoxy compounds of the formula (I) (wherein both $Z_1$ and $Z_2$ are hydrogen) by treating them with an organic peracid; to perform this reaction the compound of the formula (III) is dissolved in an inert solvent, preferably benzene or ether and then reacted with the organic peracid, preferably with perbenzoic acid or m-chloro-perbenzoic acid at a temperature between −5° C and 30° C, preferably between 10° and 20° C. The acidic reaction mixture is then neutralized by repeating washing first with an aqueous inorganic or organic base, preferably with an aqueous 10% sodium hydroxide solution and then with water; the separated organic phase is then dried and evaporated. The desired diepoxy compound of the formula (I) is obtained as evaporation residue and may be purified by recrystallization.

(b) Compounds of the formula (III), wherein both $R_1$ and $R_2$ are hydroxy groups, are treated first with an organic sulfonic acid chloride in the presence of an organic tertiary base, to yield a mixture of the corresponding 5α-hydroxy-6β-chloro and 5α,6α-epoxy compounds of the formulas (IIA) and (IIB), respectively. This reaction is performed by dissolving the compound of the formula (IA) in an organic base, preferably in pyridine, or in a mixture of an organic base and a chlorinated hydrocarbon, preferably of triethylamine and chloroform and adding an organic sulfonic acid chloride, preferably methane sulfonic acid chloride to the solution at a temperature between −10° and 50° C, preferably at 20° to 30° C. After the reaction is complete, the reaction mixture is poured into ice water and extracted with a water-immiscible solvent, preferably with dichloromethane or ether. The separated organic phase is then washed with water to neutrality, dried and evaporated. The residue is the mixture of the corresponding compounds of the formula (IIA) and (IIB), respectively. These two compounds may be either separated, or one of them may be converted into the other to yield a uniform product containing only one compound of the formula either (IIA) or (IIB). By acidifying the mixture to pH 2 - 3 e.g. with hydrochloric acid dissolved in ether, the epoxy ring is split off and the mixture is converted into the single compound of the formula (IIA); by making the mixture of alkaline to pH 8 - 9, e.g. an alcoholic, preferably methanolic solution of a base, e.g. of pyridine or sodium hydroxide, the compound (IIA) is converted into 5α,6α-epoxide and the product will be the single compound of the general formula (IIB).

The thue-obtained intermediate compound of the formula (IIA) or (IIB) is then treated with an organic peracid to yield the corresponding final product of the formula (I) ($Z_1$ = OH, $Z_2$ = Cl or $Z_1Z_2$ = epoxy). This last reaction step is performed in the same way as in the case of the epoxidation of the compound of the formula (III) ($R_1$ = H, $R_2$ = H): the compound (IIA) or (IIB) is dissolved in an inert solvent, e.g. in benzene or chloroform and then reacted with the organic peracid, preferably with perbenzoic acid or m-chloro-perbenzoic acid at a temperature between −5° C and 30° C, preferably between 10° and 20° C. The acidic reaction mixture is then neutralized by repeated washing first with an aqueous inorganic or organic base, preferably with an aqueous 10% sodium hydroxide solution and then with water; the separated organic phase is then dried and evaporated. The desired diepoxy compound of the formula (I) is obtained as evaporation residue and may be purified by recrystallization.

As described, the compounds of the present invention can be used to make the compounds of the formulas (I) (Ia) and (Ib) of Ser. No. 709,325, corresponding to compounds of the types represented in formulas (VI), (VIa) and (VIb) below:

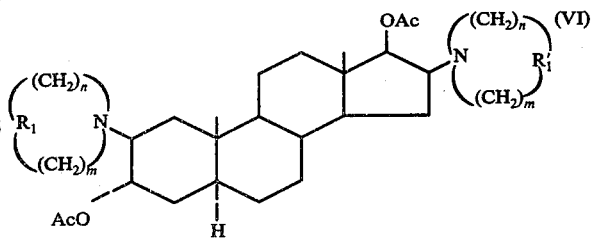

wherein
Ac is alkylcarbonyl containing 1 to 4 carbon atoms in the alkyl moiety, and one of
$R_1$ and $R_1'$ is methylene and the other is an $NR_2$ group wherein,
$R_2$ is $C_{1-3}$ alkyl
n is 1 or 2 and
m is 1, 2, 3 or 4.

The di-quaternary salts of these diaminoandrostanes have the formula

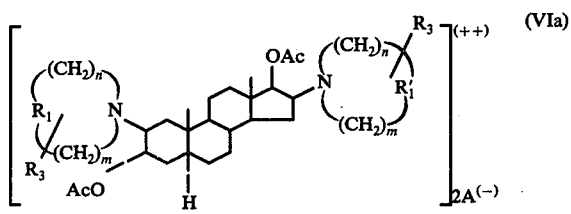

wherein

Ac, $R_1$, $R_1'$, n and m have the same meanings as defined in formula (VI),

A is halogen and $R_3$ is alkyl having 1 to 3 carbon atoms or is allyl.

The mono-quaternary salts of the compounds of the formula (VI) have the general formula

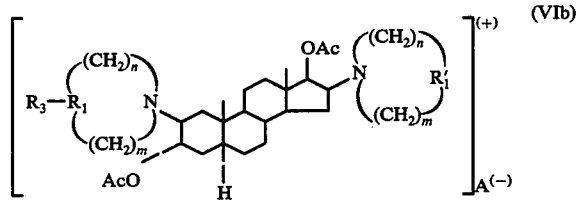

wherein

Ac, n, m, A and $R_3$ have the same meanings as in formulae VI and VI(a), $R_1$ is methylene and $R_1$ is a $<N-R_2$ group, wherein $R_2$ has the same meaning as defined for formula VI.

The compounds of the formula VI are biologically active, and the quaternary salts of the formulae VX(a) and VI(b) are outstanding curare-type compounds. The intensity of their activity surpasses the activity of the known compounds of similar effect.

Compounds of the formulae VI(a and VIb show curare type, non-depolarizing neuro-muscular blocking effect, i.e. they inhibit the inplant of the nervous impulse on the striated muscle, do not cause histamine release, do not decrease blood pressure and their effect can be stopped by neostigmine. The compounds do not show any hormonal effect.

To determine the intensity and the duration of the activity, cats subjected to anaesthesia and artificial respiration were tested.

The peroneus nerve was irritated electrically and the contraction of the bibialis muscle was registered, by intravenous administration of different doses of the blocking substances the dose inhibiting completely the muscle contraction ($ED_{100}$) was determined. The time between the starting effect and the restoration of the normal muscle reaction was measured. The data of the following table are related to the dose causing complete inhibition. As a reference substance pancuronium bromide (Negwer, 1971, P. 4821) was used. (Advances in Steroid Biochemistry and Pharmacology (Briggs), W. R. Buckett: Aspects of the Pharmacology of Aminosteroids, p. 56-59, Br. J. Pharmac. Chemother. 32, 671-682 (1968), *ArzneimittelForsch.* 19, 1723-1726 (1969).

| Compound | $ED_{100}$/mcg/kg | duration of effect/minutes |
|---|---|---|
| 2β-(4-Dimethyl-piperazino)-16β-N-methyl-piperidino-3α,17β-diacetoxy-5α-androstane-dibromide | 4.5 | 16 |
| 2β-N-Methyl-piperidino-16β-(4-dimethyl-piperazino)-3α,17β-diacetoxy-5α-androstane-dibromide | 7.2 | 18 |
| Pancuronium bromide | 18.0 | 23 |

The foregoing table shows, that the effective doses of the new curare-type compounds are 2.5 to 4 times smaller than that of pancuronium bromide and the duration of the effect is about 30 to 40% shorter.

The new curare-type compounds are used for facilitating intubation, alleviating muscle spasms in shock therapy or for hypomyotomia in any spasmodic diseases of the striated muscles.

The process of the invention is illustrated in more details by the following examples, without being limited thereto:

EXAMPLE 1

(a) 5α-Androst-2-ene-17β-hydrazone 200 g. (0.735 mol.) of 17-oxo-5α-androst-2-ene are dissolved in 2000 ml. of ethanol and then 360 ml. of triethyl amine and 880 ml. (14.7 mol.) of 98% hydrazine hydrate are added to the solution. The reaction mixture is refluxed for 2 hours and then cooled to room temperature and poured into 20 liters of ice water under vigorous stirring. The precipitated product is separated by filtration, washed with water to remove traces of triethyl amine and then dried at room temperature over phosphorous pentoxide. The crude product is recrystallized from n-hexane. 185 g. 5α-androst-2-ene-17-hydrazone (91%) are obtained; m.p. 124°-125° C; $[\alpha]_D^{25} = +98°$ ($c = 1$ in chloroform)

Analysis for $C_{19}H_{30}N_2$: calculated: C 79.60%, H 10.50%, N 9.70%; found: C 79.42%, H 10.60%, N 9.61%.

(b) 17-Bromo-5α-androsta-2,16-diene 30 g. (0.100 mol.) of 5α-androst-2-ene-17-hydrazone are dissolved in 200 ml. of anhydrous pyridine and the solution cooled to −10° C. 30 g. (0.168 mol.) of N-bromosuccinimide dissolved in 330 ml. of pyridine are then added at a temperature between 0° and −10° C to the solution. The reaction mixture is stirred until the evolution of nitrogen has ceased and then poured into 3 liters of 5% icy hydrochloric acid solution. The separated product is extracted with 300–400 ml. of carbon tetrachloride and the carbon tetrachloride phases are combined. The combined carbon tetrachloride solution is washed with aqueous 5% hydrochloric acid solution, then with water to pH = 7. The neutral carbon tetrachloride solution is dried over sodium sulfate, filtered and evaporated to dryness. The oily evaporation residue is triturated with 100 ml. of n-hexane, and the precipitated by-product is filtered off. The filtrate is evaporated to dryness and the evaporation residue is triturated with 50 ml. of a 9:1 mixture of ethanol and acetone. The solid product is filtered off and dried. 23.4 g. of 17-bromo-5α-androsta-2,16-diene (66%) are obtained; m.p. 76°-77° C; $[\alpha]_D^{25} = +71.2°$ ($c = 1$ in chloroform).

Analysis for $C_{19}H_{27}Br$: calculated: c 71.35%, H 8.07%, Br 23.80%; found: C 71.21%, H 8.15%, Br 23.57%.

17-Iodo-5α-androsta-2,16-diene is prepared in the same way from 5α-androst-2-ene-17-hydrazone as described in the previous paragraph, but instead of N-bromo-succinimide N-iodo-succinimide is used in the same molar proportion.

Yield 66%; m.p. 71°–72° C; $[α]_D^{25} = +56.3°$ ($c = 1$ in chloroform).

Analysis for $C_{19}H_{27}J$: calculated: C 59.70%, H 7.07%, I 33.13%; found: C 59.52%, H 6.90%, I 32.9%.

(c) 2α, 3α; 16α, 17α-Diepoxy-17β-bromo-5α-androstane 90 g. (0.27 mol.) of 17-bromo-5α-androsta-2,16-diene are dissolved in 1100 ml. of chloroform and 1600 ml. of a 7.2% chloroform solution of 0.81 mol. of m-chloroperbenzoic acid are added thereto. The reaction mixture is allowed to stand at room temperature for 24 hours, then chilled to 0° C and the ice-cooled mixture is washed with aqueous 10% sodium hydroxide solution and then with water to pH = 7. After separating the phases, the chloroform phase is dried over sodium sulfate, filtered and evaporated to dryness. The obtained oily evaporation residue is triturated with 100 ml. of ether, filtered and the solid crude product is recrystalized from acetonitrile. 85.7 g. of 2α, 3α; 16α, 17α-diepoxy-17β-bromo-5α-androstane (87%) are obtained; m.p. 160°–162° C; $[α]_D^{25} = +73.5°$ ($c = 1$ in chloroform).

Analysis for $C_{19}H_{27}BR_2$: calculated: C 62.00%, H 7.35%, Br 21.26%; found: C 61.79%, H 7.20%, Br 21.7%.

EXAMPLE 2

(a) 5α,6β-Dihydroxy-androst-2-ene-17-hydrozone 50 g. (0.164 mol.) of 5α, 6β-dihydroxy-17-oxo-androst-2-ene are dissolved in the mixture of 550 ml. of ethanol and 93 ml. of triethylamine, and 163 ml. (3.28 mol.) of 98% hydrazine hydrate are added to the solution. The reaction mixture is refluxed for 2 hours, then the ethanol is distilled off. The evaporation residue (300 ml.) is triturated with ether cooled previously to 0° C, the separating product is filtered, washed with ether and subsequently with water to remove the traces of triethyl amine. The product is dried over phosphorous pentoxide under reduced pressure and may be recrystalized from methanol. 50 g. of 5α, 6β-dihydroxy-androst-2-ene-17-hydrazone are obtained; m.p. 230°–232° C; $[α]_D^{25} = +44.1°$ ($c = 1$ in chloroform).

Analysis for $C_{19}H_{30}N_2O_2$: calculated: C 72.0%, H 9.43%, N 8.80%; found: C 71.8%, H 9.18%, N 9.00%.

The 5α, 6β-dihydroxy-17-oxo-androst-2-ene used as starting material can be prepared in the following way:

250 g. (0.87 mol) of 3β-hydroxy-17-oxo-androst-2-ene are dissolved in 2500 ml. of chloroform, and 198 g. (1.01 mol.) of 88% m-chloro-perbenzoic acid are added to the solution. The reaction mixture is stirred one hour at a temperature below 30° C, and then the solution of 75 g. of sodium hydroxide in 5 liters of water is added thereto. After stirring, the phases are separated. The chloroform phase is shaken out with a further portion of the sodium hydroxide solution to bring the pH value to 7, then washed with water and the phases are separated again. The chloroform phase is dried over sodium sulfate and the chloroform is distilled off. A mixture of 3β-hydroxy-5α, 6α-epoxy-17-oxo-androstane and 3β-hydroxy-5β,6β-epoxy-17-oxo-androstane is obtained as evaporation residue. This mixture of isomers is stirred with a 10-fold amount of ether and then filtered. 234 g. of this mixture of isomers (90%) is obtained; m.p. 197°–200° C.

Analysis for $C_{19}H_{28}O_3$: calculated: C 75.00%, H 9.22%; found: C 74.70%, H 8.98%.

275 g. (0.905 mol.) of the above obtained mixture isomers are dissolved in 2150 ml. of dioxane. In approximately 20 minutes 725 ml. of 10% perchloric acid solution are added to the said solution at 20°–30° C. The reaction mixture is stirred at room temperature for 1.5 hours, then poured into 7 liters of icy 20% sodium chloride solution. The precipitated product is filtered and washed with 500 ml. of water. The filtrate is saturated with sodium chloride and allowed to stand over night at a temperature between 0° and 5° C. The separating second crop of the product is filtered off and combined with the bulk of the product. The so-obtained product is purified by mixing with 10-fold amount of ether. 263 g. of 3β,5α,6β-trihydroxy-17-oxo-androstane (95%) are obtained in this way, m.p. 304°–306° C.

Anaylsis for $C_{19}H_{30}O_4$: calculated: C 70.80%, H 9.33%; found: C 70.71%, H 9.08%.

100 g (0.31 mol.) of the above obtained trihydroxy compound are dissolved in 1000 ml. of anhydrous pyridine, and 89 g. (0.466 mol.) p-toluene-sulfonic acid chloride are added to the solution. The reaction mixture is allowed to stand for 48 hours at a temperature between 0° and 5° C, and then poured into 10 liters of ice water. The separated product is filtered off, washed with an aqueous 3–4% hydrochloric acid solution and subsequently with water until the last traces of pyridine are removed, and then dried at max. 40° C in vacuo over phosphorous pentoxide. The product may be purified, if desired, by mixing with a 10-fold amount of ether. 138 g. of 3β-tosyloxy-5α,6β-dihydroxy-17-oxo-androstane (93%) are obtained; m.p. 154°–156° C; $[α]_D^{25} = 0°$ ($c = 1$ in chloroform).

Analysis for $C_{26}H_{36}O_6S$: calculated: C 65.40%, H 7.55%, S 6.70%; found: C 65.41%, H 7.29%, S 6.50%.

70 g (0.147 mol) of the above-obtained 3β-tosyloxy-5α,6β-dihydroxy-17-oxo-androstane are dissolved in 350 ml. of collidine and the reaction mixture is heated in a nitrogen atmosphere, under stirring for 1.5 hours in an oil bath of 160° C. The collidine is then distilled off under reduced pressure, the evaporation residue is triturated with 400 ml. of water, filtered and washed with 10% aqueous hydrochloric acid solution, then with water to remove the last traces of collidine. The so-obtained product is dried in vacuo over phosphorous pentoxide at 40° C, and may be purified, if desired, by mixing with a fivefold amount of diethyl ether. 45 g of 5α,6β-dihydroxy-17-oxo-androst-2-ene (90%) are obtained; m.p. 183°–186° C; $[α]_D^{25} = +81°$ ($c = 1$ in chloroform).

Analysis for $C_{19}H_{28}O_3$: calculated: C 75.00%, H 9.22%; found: C 75.10%, H 9.07%.

(b) 5α,6β-Dihydroxy-17-bromo-androsta-2,16-diene

This compound is prepared from 290 g (0.91 mole) of 5α,6β-dihydroxy-androst-2-ene-17-hydrazone and 186 g (1.23 moles) of N-bromo-succinimide, as described in section (b) of Example 1, but with the difference that after pouring the reaction mixture into icy hydrochloric acid solution, the obtained product is agitated with a 40-fold amount of ether. The undissolved by-product is filtered off, the ether solution is evaporated and the obtained oily residue is purified by mixing it with 250 ml of n-hexane. The crystalline product is filtered off and dried. 130 g of 5α,6β-dihydroxy-17-bromo-androsta-2,16-diene (38%) are obtained; m.p. 170°–175° C; $[α]_D^{25}$ = +25.1 ($c$ = 1 in chloroform).

Analysis for $C_{19}H_{27}BrO_2$: calculated: C 62.20%, H 7.35%, Br 21.8%; found: C 62.00%, H 7.12%, Br 21.6%.

(c)

5α-Hydroxy-6β-chloro-17-bromo-androsta-2,16-diene 95 g (0.258 mole) of 5α,6β-dihydroxy-17-bromo-androsta-2,16-diene are dissolved in 950 ml of anhydrous pyridine, and 21 ml (0.276 mole) of methanesulfonic acid chloride are added under stirring at room temperature to the solution. The reaction mixture is allowed to stand for 16 hours and then poured under vigorous stirring into 9 liters of ice water. The precipitating difficulty separable substance is extracted with 1600 ml of dichloro methane. The dichloro methane extract is washed with aqueous 10% hydrochloric acid solution to remove the pyridine and then with water until neutral, dried over sodium sulfate and evaporated to dryness. The evaporation residue, which is a mixture of 5α-hydroxy-6β-chloro-17-bromo-androsta-2,16-diene and 5α,6β-epoxy-17-bromo-androsta-2,16-diene, is dissolved in diethyl ether and etheral hydrochloric acid solution is added thereto until pH = 2 to 3. The so obtained 5α-hydroxy-6β-chloro-17-bromo-androsta-2,16-diene is separated and purified by mixing it with 10-fold amount of petroleum ether. 79.0 g of 5α-hydroxy-6β-chloro-17-bromo-androsta-2,16-diene (79.0%) are obtained; m.p. 125°–126° C; $[α]_D^{25}$ = +3.8° ($c$ = 1 in chloroform).

Analysis for $C_{19}H_{26}BrClO$: calculated: C 59.10%, H 6.73%, Br 20.62%, Cl 9.17%; found: C 59.30%, H 6.51%, Br 20.37%, Cl 8.70%.

(d)

2α,3α;16α,17α-Diepoxy-5α-hydroxy-6β-chloro-17β-bromo-androstane 42 g (0.109 mole) of 5α-hydroxy-6β-chloro-17-bromo-androsta-2,16-diene are dissolved in 360 ml of chloroform, and 915 ml (0.332 mole) of 5% perbenzoic acid solution in chloroform are added thereto. The reaction mixture is allowed to stand at room temperature for 16 hours, then washed at a temperature between 0° and 5° C with 10% aqueous sodium hydroxide and then with water until pH = 7. The phases are separated, the chloroform phase is dried over sodium sulfate, filtered and evaporated to dryness. The evaporation residue is recrystallized from acetonitrile. 43 g of 2α,3α;16α,17α-diepoxy-5α-hydroxy-6β-chloro-17β-bromo-androstane (94%) are obtained; m.p. 150°–152° C; $[α]_D^{25}$ = +19.5° ($c$ = 1 in chloroform).

Analysis for $C_{19}H_{26}BrClO_3$: calculated: C 54.60%, H 6.22%, Br 19.10%, Cl 8.50% found: C 54.41%, H 6.00%, Br 18.79%, Cl 8.30%.

EXAMPLE 3

(a) 5α, 6α-Epoxy-17-bromo-androsta-2,16-diene 95 g (0.258 mole) of 5α,6β-dihydroxy-17-bromo-androsta-2,16-diene obtained as described in section (b) of Example 2 are reacted with 21 ml (0.276 mole) of methanesulfonic acid chloride, as described in section (c) of Example 2, but with the difference that the mixture of products obtained after evaporation of the dichloro methane extract is dissolved in 16-fold amount (calculated on the starting material) of ethanol and the 12% aqueous solution of 19 g of sodium hydroxide is added to the ethanolic solution. The reaction mixture is heated to reflux for 10 minutes, then cooled to room temperature and the pH value is adjusted to 7 with acetic acid. The solvent is then distilled off, the evaporation residue is triturated with water. The precipitated product is filtered off, washed with water until the washings are neutral and dried over phosphorous pentoxide in vacuo. The obtained product is recrystallized from acetonitrile. Yield: 89% of 5α,6α-epoxy-17-bromo-androsta-2,16-diene; m.p. 146°–147° C; $[α]_D^{25}$ = −18.3° ($c$ = 1 in chloroform).

Analysis for $C_{19}H_{25}BrO$: calculated: C 65.40%, H 7.16%, Br 22.80%; found: C 65.20%, H 6.98%, Br 22.57%.

(b)

2α,3α;5α,6α;16α,17α-Triepoxy-17β-bromo-androstane 19.5 g (0.056 mole) of 5α,6α-epoxy-17-bromo-androsta-2,16-diene are dissolved in 125 ml of chloroform, and 460 ml (0.168 mole) of 5% solution of perbenzoic acid in chloroform are added thereto. The reaction mixture is allowed to stand for 16 hours at room temperature, then cooled to a temperature between 0° and 5° C, washed with 10% aqueous sodium hydroxide solution and then dried with water until pH = 7. The chloroform phase is separated, dried over sodium sulfate, filtered and evaporated to dryness. The evaporation residue is triturated with 10-fold amount of ether and the obtained product is recrystallized from acetonitrile. 20 g of 2α,3α;5α,6α;16α,17α-triepoxy-17β-bromo-androstane (94%) are obtained; m.p. 206°–209° C; $[α]_D^{25}$ = +33.3° ($c$ = 1 in chloroform).

Analysis for $C_{19}H_{25}BrO_3$: calculated: C 59.80%, H 6.60%, Br 20.94%; found: C 59.68%, H 6.91%, Br 20.70%.

Preparation of Curare-Type Compounds

The products of the foregoing Examples are converted into curare-type compounds as described in Ser. No. 709 323 and Ser. No. 709 325.

EXAMPLE 4

2α,3α;5α,6α-Diepoxy-17-oxo-16β-piperidine-androstane (a) 13.5 g (0.032 mole) of 2α,3α;16α,17α-diepoxy-5α-hydroxy-6β-chloro-17β-bromo-androstane (Example 2 (d)) are dissolved in 100 ml of acetonitrile and 11 ml (0.111 mole) of piperidine are added. The reaction mixture is heated for 1 hour under reflux and is evaporated at reduced pressure. The residue is dissolved in chloroform, washed with a solution of sodium chloride and water until a pH value of 7 to 7.5 is achieved. The two layers are separated. The chloroform layer is dried over sodium sulfate, filtered and the filtrate is evaporated to dryness. The crystalline residue is purified by admixing it with ether, the mixture is filtered and dried. Yield: 10.3 g (82.6%) of 2α,3α;5α,6α-diepoxy-17-oxo-16β-piperidine-androstane; m.p. 187°–190° C; $[α]_D^{25}$ = +31.7° ($c$ = 1 chloroform).

Analysis for $C_{24}H_{35}NO_3$: calculated: C 74.80%, H 9.11%, N 3.64%; found: C 74.59%, H 8.97%, N 3.47%.

(b) 6.0 g (0.157 mole) of 2α,3α;5α,6α;16α,17α-triepoxy-17β-bromo-androstane (Example 3(b)) are dissolved in 45 ml of aceto nitrile and 6.4 ml (0.0647 mole) of piperidine are added. The reaction mixture is heated under reflux for 1 hour and evaporated at reduced pressure. The residue is dissolved in ether whereafter the ethereal solution is washed first with a saturated sodium chloride solution then with water. The 2 layers are separated, the water is removed from the ether layer with sodium sulfate; and the residue is filtered. The residue is triturated with ether cooled to 0° C; the precipitated product is filtered, and dried. The physical constants and the product are identical with those given in Example 4(a).

EXAMPLE 5

2α,3α;5α,6α-Diepoxy-17β-hydroxy-16β-piperidino-androstane 8 g (0.0208 mole) of 2α,3α;5α,6α-diepoxy-17-oxo-16β-piperidino-androstane are dissolved in 36 ml of tetrahydrofuran and 15 ml of methanol and a suspension of 5 g (0.132 mole) of sodium borohydride in 9 ml of water are aded. The reaction mixture is stirred for 8 hours, and evaporated to dryness at a temperature of below 40° C. The residue is triturated with water and the precipitated crude product is filtered, the precipitation is purified with ether, filtered and dried. Yield: 6.4 g (79.5%) of 2α,3α;5α,6α-diepoxy-17β-hydroxy-16β-piperidino-androstane. M.p.: 184°-188° C; $[\alpha]_D^{25}$ = −42.7° ($c$ = 1 in chloroform).

Analysis for $C_{24}H_{37}NO_3$: calculated: C 74.40%, H 9.55%, N 3.62 found: C 74.18%, H 9.50%, N 3.47%.

EXAMPLE 6

2β,6β,16β-Tripiperidino-3α,5α,17β-trihydroxy-androstane 6 g (0.0155 mole) of 2α,3α;5α,6α-diepoxy-17β-hydroxy-16β-piperidino-androstane (Example 5) are dissolved in a mixture of 60 ml (0.606 mole) of piperidine and 10 ml of water. The reaction mixture is heated in a bomb tube for 72 hours at an outer temperature of 140° C. After the reaction is complete, the reaction mixture is evaporated to dryness, the residue is triturated with ether and the precipitated crystalline product is filtered and heated in acetonitrile under reflux. The purified product is filtered and dried. Yield: 6.7 g (78.5%) of 2β,6β,16β-tripiperidino-3α,5α,17β-trihydroxy-androstane; $[\alpha]_D^{25}$ = +19.3° ($c$ = 1 in chloroform).

Analysis of $C_{34}H_{55}N_3O_3$: calculated: C 73.70%, H 9.95%, N 7.60%; found: C 73.58%, H 9.75%, N 7.42%.

EXAMPLE 7

2β,6β,16β-Tripiperidine-3α,17β-diacetoxy-5α-hydroxy-androstane

The compound is prepared from 2β,6β,16β-tripiperidino-3α,17β-trihydroxy-androstane (Example 6), in that 0.0029 mole is dissolved in a mixture of 9 ml of acetic acid anhydride and 0.6 ml of glacial acetic acid and 0.3 g of zinc chloride are added. The reaction mixture is stirred at room temperature for 12 hours and 30 ml of water are added to the mixture and it is stirred for another 2 hours. The aqueous solution is cooled to 0° to 5° C and the pH is adjusted at the same temperature to 8-10 by adding a 10% aqueous sodium hydroxide solution. The precipitated fluffy substance is immediately extracted with ether. The ether extract is washed with saturated sodium chloride and/or water to achieve pH = 7. The layers are separated. The ether phase is dried over sodium sulfate, filtered and evaporated to dryness. The residue is dissolved in ether, clarified with silica gel and the silica gel is removed from the mixture by filtration. The filtrate is evaporated to dryness and the residue is, if desired, triturated with n-hexane, filtered and dried. Yield: 1.7 g (75.5%) of 2β,6β,16β-tripiperidino-3α,17β-diacetoxy-5α-hydroxy-androstane; m.p. 150°-153° C; $[\alpha]_D^{25}$ = −3.3° ($c$ = 1 in chloroform).

Analysis for $C_{38}H_{55}N_6O_5$: calculated: C 66.40%, H 9.62%, N 12.22%; found: C 66.25%, H 9.31%, N 12.05%.

Yield: 77.0% of 2β,6β,16β-tripiperidino-3α,17β-diacetoxy-5α-hydroxyandrostane; m.p. 104°-105° C (decomposition); $[\alpha]_D^{25}$ = −7.3° ($c$ = 1 in chloroform).

Analysis for $C_{38}H_{59}N_3O_5$: calculated: C 71.60%, H 9.27%, N 6.60%; found: C 71.50%, H 9.00%, N 6.38%.

EXAMPLE 8

2β,11β-bis-N-Methyl-piperidino-3α,17β-diacetoxy-5α-hydroxy-androstane-dibromide 0.5 g (0.785 mole) of 2β,6β,16β-tripiperidino-3α,17β-diacetoxy-5α-hydroxy-androstane (Example 7) are dissolved in 20 ml of acetone whereafter 20 ml of 8% solution of methyl bromide (16.9 mole) in acetone are added. The reaction mixture is allowed to stand for 1 week at room temperature followed by precipitating the product by dilution with ether. The precipitated diquaternary product is filtered, washed with acetone at a temperature of 5°-10° C and dried. Yield: 0.6 g (92%) of 2β,16β-bis-N-methyl-piperidino-6β-piperidino-3α,17β-diacetoxy-5α-hydroxy-androstane-dibromide (a curare-like compound used as described); m.p. 187° C (decomposition); $[\alpha]_D^{25}$ = +2.9° ($c$ = 1 in chloroform).

Analysis of $C_{40}H_{65}Br_2N_3O_5$: calculated: C 58.00%, H 7.85%, Br 19.22%, N 5.06%; found: C 57.78%, H 7.90%, Br 18.92%, N 5.10%.

EXAMPLE 9

2α,3α-epoxy-17-oxo-16β-N-methyl-piperazino-5α-androstane 25 g (0.068 mole) of 2α,3α;16α,17α-diepoxy-17β-bromo-5α-androstane (Example 1(c)) are dissolved in 170 ml of acetonitrile, whereafter 20.5 ml (0.190 mole) of N-methyl-piperazine are added. The reaction mixture is allowed to stand for 24 hours and heated under reflux for 15 minutes. The reaction mixture is evaporated to dryness at reduced pressure and the residue is dissolved in methylene chloride. The methylene chloride solution is washed with water until the pH achieves the value of 7, followed by the separation of the two layers. The organic layer is dried over sodium sulfate, filtered and the filtrate is evaporated at reduced pressure. The residue is purified by stirring with ether, the crystallized product is filtered and dried. Yield: 20.1 g (76.5%) of 2α,3α-epoxy-17-oxo-16β-N-methyl-piperazino-5α-androstane; m.p. 132°-134° C; $[\alpha]_D^{25}$ = +121.2° ($c$ = 1 in chloroform).

Analysis for $C_{24}H_{38}N_2O_2$: calculated: C 74.60%, H 9.85%, N 7.24%; found: C 74.39%, H 9.97%, N 7.12%.

EXAMPLE 10

2α,3α-epoxy-17β-hydroxy-16β-N-methyl-piperazino-5α-androstane 15 g (0.038 mole) of 2α,3α-epoxy-17-oxo-16β-N-Methyl-piperazino-5α-androstane (Example 9) are dissolved in the mixture of 45 ml of methylene chloride and 120 ml of methanol, whereafter 12 g (0.31 mole) of sodium borohydride are added at a temperature of below 30° C. When the addition is complete, the product of the reduction is crystallized. The crystalline solution is stirred vigorously for 12 hours, whereafter the solvent is distilled at reduced pressure at a temperature of below 40° C. The residue is triturated with water, the crystallized product is filtered, dissolved in chloroform and washed with 5% aqueous sodium hydroxide solution and with water until pH = 7. The layers are separated. The chloroform layer is dried on sodium sulfate, filtered and the filtrate is evaporated to dryness. The residue is recrystallized from acetonitrile. Yield: 11.7 g (77.2%) of 2α,3α-epoxy-17β-N-methyl-piperazino-5α-androstane; m.p. 149°–153° C; $[\alpha]_D^{25} = +27.1°$ ($c = 1$ in chloroform).

Analysis for $C_{24}H_{40}N_2O_2$: calculated: C 74.20%, H 10.30%, N 7.22%; found: C 74.01%, H 10.41%, N 7.07%.

EXAMPLE 11

2β-piperidino-16β-N-methyl-piperazino-3α,17β-dihydroxy-5α-androstane 14.8 g (0.03 mole) of 2α,3α-epoxy-17β-hydroxy-16β-N-methyl-piperazino-5α-androstane (Example 10) are dissolved in 168 ml (1.65 moles) of piperidine and 24 ml of water, whereafter the reaction mixture is heated in a bomb tube of 72 hours at a temperature of 140° C. After the reaction is accomplished the reaction mixture is evaporated at reduced pressure. The residue is stirred in acetonitrile, filtered and the product above the filter is heated under reflux in acetonitrile. The crystallized product is filtered and dried. Yield: 12.4 g (69.0%) of 2β-piperidino-16β-N-methyl-piperazino-3α,17β-dihydroxy-5α-androstane; m.p. 154°–156° C; $[\alpha]_D^{25} = +84.5°$ ($c = 1$ in chloroform).

Analysis for $C_{29}H_{51}N_3O_2.H_2O$: calculated: C 71.0%, H 10.80%, N 9.26%; found: C 70.8%, H 10.97%, N 9.10%.

EXAMPLE 12

2β-piperidino-16β-N-methyl-piperazino-3α,17β-diacetoxy-5α-androstane 3 g (0.0063 mole) of 2β-piperidino-16β-N-methyl-piperazino-3α,17β-dihydroxy-5α-androstane (Example 11) are dissolved in the mixture of 13 ml of acetic acid anydride and 1 ml of glacial acetic acid, whereafter 0.3 g of zinc chloride is given to the solution. The reaction mixture is stirred for 12 hours, whereafter the excess acetic acid anhydride is decomposed by adding 40 ml of water. The solution is cooled to 0° to 5° C and 15% aqueous sodium hydroxide solution is added at the same temperature until the pH achieves the value of 9–10. The precipitated fluffy substance is immediately extracted with ether. The ether extract is washed with an aqueous solution saturated with sodium chloride until a neutral state is achieved. The layers are separated, the ether layer is dried over sodium sulfate and filtered. The filtrate is treated with 3 g of decolorizing silica gel, the mixture is filtered and evaporated to dryness. The product is crystallized from the residue by trituration with n-hexane, filtered and dried. Yield: 2.6 g (73.5%) of 2β-piperidino-16β-N-methyl-piperazino-3α,17β-diacetoxy-5α-androstane; m.p. 95°–98° C; $[\alpha]_D^{25} = +33.9°$ ($c = 1$ in chloroform).

Analysis of $C_{33}H_{55}N_3O_4$: calculated: C 71.20%, H 9.00%, N 7.54%; found: C 71.01%, H 8.87%, N 7.36%.

EXAMPLE 13

2β-N-methyl-piperidino-16β-(4-dimethyl-piperazino)-3α,17β-diacetoxy-5α-androstane-dibromide 1 g (0.0018 mole) of 2β-piperidino-16β-N-methyl-piperazino-3α,17β-diacetoxy-5α-androstane (Example 12) is dissolved in 20 ml of acetone whereafter 10 ml of 5% solution of methyl bromide in acetone is added. The reaction mixture is allowed to stand for 48 hours at room temperature. The precipitated quaternary salt is filtered, triturated with acetone and ether and filtered. The filtered precipitation is heated under reflux in acetone, the crystalline solution is cooled to room temperature, filtered and dried. Yield: 1.2 g (87.2%) of 2β-N-methyl-piperidino-16β-(4-dimethyl-piperazino)-3α,17β-diacetoxy-5α-androstane-dibromide (a curare-like compound with utility and effect as described); m.p. 260°–264° C (decomposition).

Analysis of $C_{35}H_{61}N_3BrO_4.H_2O$: calculated: C 55.00%, H 8.24%, Br 20.90%, N 5.50%; found: C 54.81%, H 8.10%, Br 20.51%, N 5.40%.

EXAMPLE 14

2β-chloro-3α-hydroxy-17-oxo-16β-piperidino-5α-androstane-hydrochloride 12.5 g (0.034 mole) of 2α,3α;16α,17α-diepoxy-17-bromo-5α-androstane (Example 1(c)) are dissolved in 85 ml of acetonitrile, whereafter 10 ml (0.1 mole) of piperidine are added. The reaction mixture is heated under reflux for 1 hour, and the reaction mixture is evaporated at reduced pressure. The residue is dissolved in diethylether and the ether solution is washed with water until pH = 7. The two layers are separated. The product is precipitated from the organic layer with 6% ethereal hydrochloric acid solution in the form of a chlorohydrate salt. The precipitated acid addition salt is filtered, washed with ether and dried in vacuo at 60° C. Yield: 10.3 g (70%) of 2β-chloro-3α-hydroxy-17-oxo-16β-piperidino-5α-androstane-hydrochloride; m.p. 237°–239° C (decomposition).

Analysis of $C_{24}H_{39}O_2NCl_2$: calculated: C 64.8 %, H 8.7%, Cl 16.0%; found: C 64.6%, H 9.0%, Cl 15.7%.

EXAMPLE 15

2β-chloro-3α,17β-dihydroxy-16β-piperidino-5α-androstane 25 g (0.056 mole) of 2β-chloro-3α-hydroxy-17-oxo-16β-piperidino-5α-androstane-hydrochloride (Example 14) are dissolved in the mixture of 52 ml of methylene chloride and 125 ml of methanol. Under vigorous stirring 2.75 g (0.069 mole) of pulverized sodium hydroxide are added at a temperature of 15°–20° C. 12.5 g (0.33 mole) of sodium borohydride are also added to the solution. The product precipitated immediately. The crystalline solution is stirred for 5 hours, whereafter the product is filtered and washed with water. The mother liquor is evaporated at reduced pressure at a temperature of below 30° C, the residue is triturated with water, the mixture is filtered and the second crop above the filter is washed with water. The two fractions are combined, dried in vacuo at 50° C, followed by recrystallization from acetone. Yield: 20.2 g (88%) of 2β-chloro-3α,17β-dihydroxy-16β-piperidine-5α-androstane; m.p. 232°–234° C.

Analysis for $C_{24}H_{40}ClO_2N$: calculated: C 70.3%, H 9.7%, Cl 8.6%; found: C 70.0%, H 9.9%, Cl 8.8%.

EXAMPLE 16

2β-N-methyl-piperazino-16β-piperidino-3α,17β-dihydroxy-5α-androstane

The compound was prepared according to Example 11 from 2β-chloro-3α,17β-dihydroxy-16β-piperidino-5α-androstane and from N-methyl-piperazine. Yield: 67.0% of 2β-N-methyl-piperazino-16β-piperidino-3α,17β-dihydroxy-5α-androstane; m.p. 230°-234° C; $[\alpha]_D^{25} = +81.7$ (c = 1 in chloroform).

Analysis for $C_{29}H_{51}N_3O_2.H_2O$: calculated: C 71.0%, H 10.8%, N 9.26%; found: C 70.8%, H 10.7%, N 9.05%.

EXAMPLE 17

2β-N-methyl-piperazino-16β-piperidino-3α,17β-diacetoxy-5α-androstane

The compound is prepared by acylation of 2β-N-methyl-piperazino-16β-piperidino-3α,17β-dihydroxy-5α-androstane according to the method described in Example 12. Yield: 72.0% $[\alpha]_D^{25} = +29.4°$ (c = 1 in chloroform).

EXAMPLE 18

2β-(4-dimethyl-piperazino)-16β-N-methyl-piperidino-3α,17β-diacetoxy-5α-androstane-dibromide 1.3 g (2.34 moles) of 2α-N-methyl-piperazino-16β-piperidino-3α,17β-diacetoxy-5α-androstane (Example 17) are dissolved in the mixture of 10 ml of acetone and 20 ml of acetonitrile. 32 ml of a solution of 8.4% methyl bromide (28 moles) in acetone are added. The reaction mixture is allowed to stand for 98 hours at room temperature and the precipitated quaternary salt is isolated by the method described in Example 13. Yield: 1.4 g (78.5%) of 2β-(4-dimethyl-piperazino)-16β-N-methyl-piperidino-3α,17β-diacetoxy-5α-androstane-dibromide; m.p. 248°-252° C (decomposition); $[\alpha]_D^{25} = -14.3°$ (c = 1 in chloroform).

Analysis for $C_{35}H_{61}Br_2N_3O_4.H_2O$: calculated: C 55.00%, H 8.24%, N 5.50%, Br 20.9%; found: C 54.75%, H 7.96%, N 5.42%, Br 20.6%.

EXAMPLE 19

2β-(4-dimethyl-piperazino)-16β-piperidino-3α,17β-diacetoxy-5α-androstane-bromide 2 g (3.6 moles) of 2β-N-methyl-piperazino-16β-piperidino-3α,17β-diacetoxy-5α-androstane (Example 17) are dissolved in 20 ml of acetone whereafter 12 ml (10.6 moles) of 8.4% methyl bromide in acetone are added. The reaction mixture is allowed to stand at room temperature, whereafter the precipitated quaternary salt is filtered, washed with acetone and ether and the precipitation is purified by mixing it with acetone, the mixture is filtered and dried. Yield: 1.5 g (62.5%) of 2β-(4-dimethyl-piperazino)-16β-piperidino-3α,17β-diacetoxy-5α-androstane-bromide; m.p. 234°-237° C (decomposition); $[\alpha]_D^{25} = +12.8°$ (c = 1 in chloroform).

Analysis for $C_{34}H_{58}BrN_3O_4.H_2O$: calculated: C 61.4%, H 8.7%, N 6.1%, Br 11.7%; found: C 61.1%, H 8.9%, N 5.9%, Br 11.3%.

What we claim is:

1. A compound of the formula

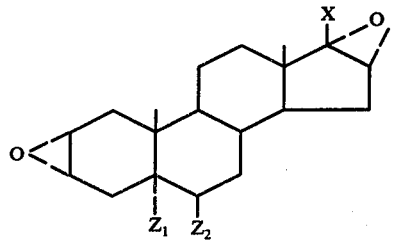

wherein
X is halogen,
$Z_1$ and $Z_2$ are both hydrogen, or $Z_1$ is hydroxy and $Z_2$ is chlorine, or
$Z_1$ and $Z_2$ together stand for an α-epoxy group.

2. The compound defined in claim 1 which is selected from the group which consists of:
2α, 3α, 5α, 6α, 16α, 17α-triepoxy-17β-bromo-androstane;
2α, 3α, 16α, 17α-Diepoxy-5α-hydroxy-6β-chloro-17β-bromo-androstane; and
2α, 3α, 16α, 17α-Diepoxy-17β-bromo-5α-androstane.

3. The compound defined in claim 1 which is 2α, 3α,5α,6α,16α, 17α-triepoxy-17β-bromo-androstane.

4. The compound defined in claim 1 which is 2α, 3α, 16α, 17α-diepoxy-5α-hydroxy-6β-chloro-17β-bromo-androstane.

5. The compound defined in claim 1 which is 2α, 3α,16α, 17α-diepoxy-17β-bromo-5α-androstane.

6. A compound of the formula:

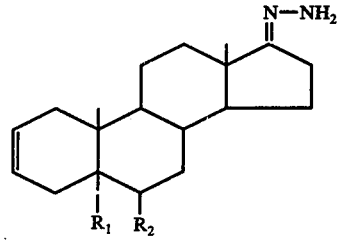

wherein $R_1$ and $R_2$ are both hydrogen or both hydroxy.

7. The compound defined in claim 6 which is 5α-androst-2-ene-17-hydrazone.

8. The compound defined in claim 6 which is 5α, 6β-dihydroxy-androst-2-ene-17-hydrazone.

9. The compound defined in claim 7 which is 17-bromo-5α-androsta-2,16-diene.

10. A process for the preparation of epoxy-androstanes of the formula:

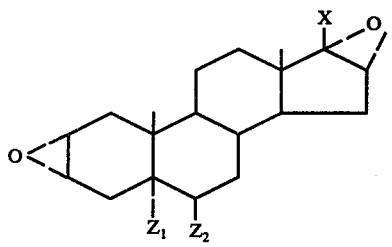

wherein
X is halogen, and
$Z_1$ and $Z_2$ are both hydrogen, which comprises the steps of:
(a) reacting a compound of the formula:

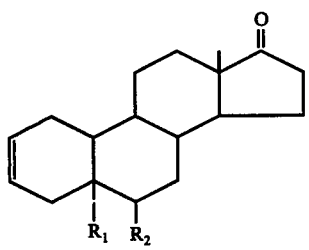

wherein $R_1$ and $R_2$ are both hydrogen, with hydrazine, (b) treating the obtained compound of the formula:

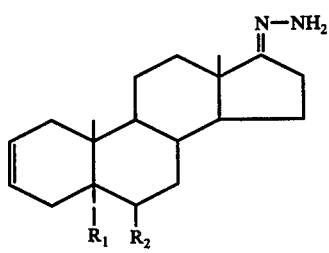

with an N-halo-succinimide to yield the corresponding compounds of the formula:

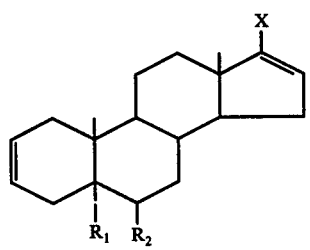

and then (c) reacting the compound with an organic peracid to yield the desired product.

11. A process for the preparation of epoxy-androstanes of the formula:

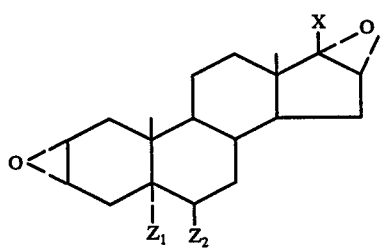

wherein
X is halogen, and
$Z_1$ is hydroxy and $Z_2$ is chorine,
which comprises the steps of:

(a) reacting a compound of the formula:

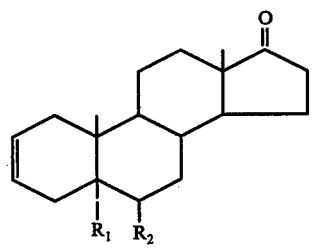

wherein $R_1$ and $R_2$ are both hydroxy, with hydrazine, (b) treating the obtained compound of the formula:

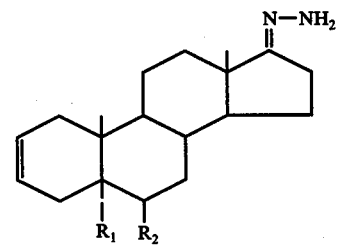

with a N-halo-succinimide to yield the corresponding compound of the formula:

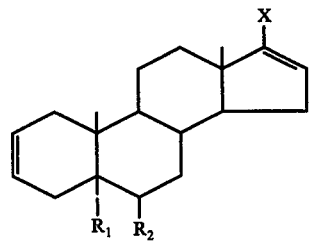

(c) reacting the compound with an organic sulfonic acid chloride, in the presence of an organic tertiary base to yield a mixture of the compounds of the formulae:

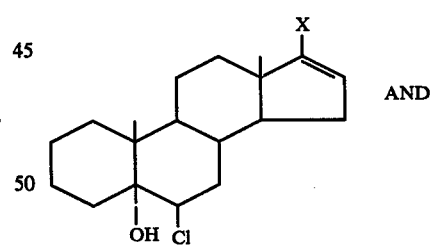

AND

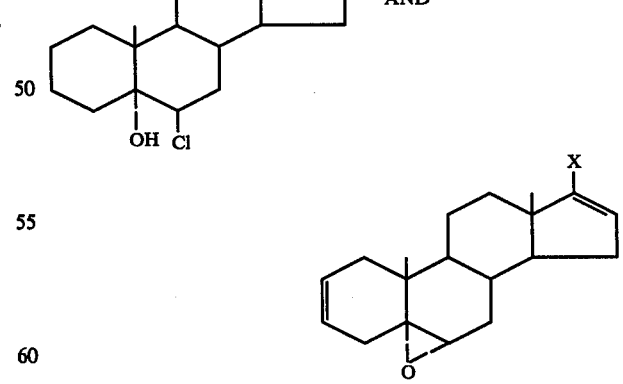

and then (d) treating the mixture of the above compounds with hydrohalic acid and subsequently with an organic peracid to yield the desired product.

12. A process for the preparation of epoxy-androstanes of the formula:

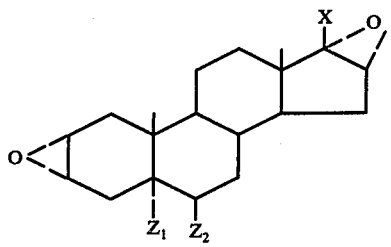

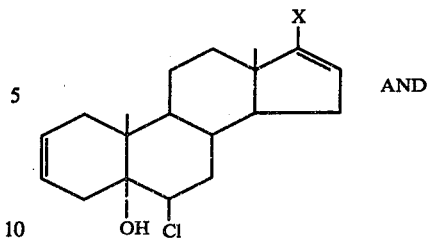

AND

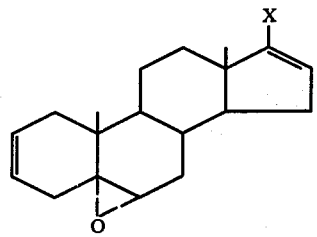

wherein
X is halogen, and
$Z_1$ and $Z_2$ together stand for an α-epoxy group, which comprises the steps of:

(a) reacting a compound of the formula:

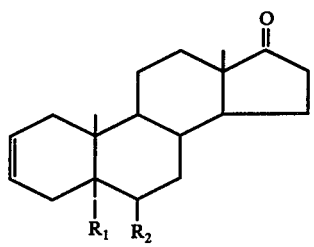

wherein $R_1$ and $R_2$ are both hydroxy, with hydrazine, (b) treating the obtained compound of the formula:

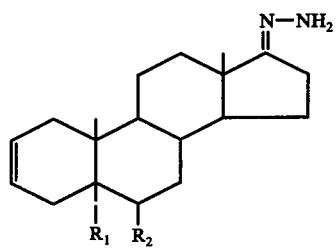

with an N-halo-succinimide to yield the corresponding compound:

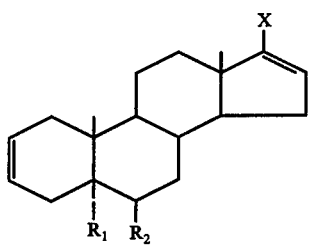

(c) reacting the compound with an organic sulfonic acid chloride, in the presence of an organic tertiary base to yield a mixture of the compounds of the formulae:

and then (d) treating the mixture of the above compounds with a base and subsequently with an organic peracid to yield the desired product.

13. The process defined in claim 10, step (a), wherein the reaction is carried out at the boiling point of the mixture of the reactants.

14. The process defined in claim 10, step (b), wherein the reaction is performed at a temperature between −30° C and 20° C.

15. The process defined in claim 10, step (c), wherein the reaction is performed at a temperature between −10° C and 50° C.

16. The process defined in claim 10 wherein the reactions are carried out in an organic solvent.

17. The process defined in claim 11, step (a), wherein the reaction is carried out at the boiling point of the mixture of the reactants.

18. The process defined in claim 11, step (b), wherein the reaction is performed at a temperature between −30° C and 20° C.

19. The process defined in claim 11, step (d), wherein the reaction is performed at a temperature between −10° C and 50° C.

20. The process defined in claim 11 wherein the reactions are carried out in an organic solvent.

21. The process defined in claim 12, step (a), wherein the reaction is carried out at the boiling point of the mixture of the reactants.

22. The process defined in claim 12, step (b), wherein the reaction is performed at a temperature between −30° C and 20° C.

23. The process defined in claim 12, step (d), wherein the reaction is performed at a temperature between −10° C and 50° C.

24. The process defined in claim 12 wherein the reactions are carried out in an organic solvent.

* * * * *